United States Patent [19]

Bolich, Jr.

[11] 4,379,753

[45] Apr. 12, 1983

[54] HAIR CARE COMPOSITIONS

[75] Inventor: Raymond E. Bolich, Jr., Maineville, Ohio

[73] Assignee: The Procter & Gamble Company, Cincinnati, Ohio

[21] Appl. No.: 267,988

[22] Filed: May 28, 1981

Related U.S. Application Data

[62] Division of Ser. No. 119,347, Feb. 7, 1980, Pat. No. 4,345,080.

[51] Int. Cl.³ .............................................. C11D 3/48
[52] U.S. Cl. .................................... 252/106; 252/547; 252/DIG. 13; 252/550; 424/70; 424/245; 424/288; 424/289
[58] Field of Search ............... 252/106, 547, DIG. 13, 252/550; 424/245, 70, 288, 289; 546/6

[56] References Cited

U.S. PATENT DOCUMENTS

| | | | |
|---|---|---|---|
| 119,283 | 2/1880 | Winkler . | |
| 119,346 | 2/1880 | Bolich et al. . | |
| 2,686,786 | 8/1954 | Shaw et al. | 546/290 |
| 2,786,847 | 3/1957 | Cislak . | |
| 2,809,971 | 10/1957 | Bernstein et al. . | |
| 3,412,033 | 11/1968 | Karsten et al. | 252/107 |
| 3,583,999 | 6/1971 | Damico . | |
| 3,590,035 | 6/1971 | Damico . | |
| 3,723,325 | 3/1973 | Parran | 252/106 |
| 3,773,770 | 11/1973 | Damico . | |
| 4,033,895 | 7/1977 | Gerstein | 252/106 |
| 4,089,945 | 5/1978 | Brinkman et al. . | |
| 4,115,315 | 9/1978 | Marinella | 252/316 |
| 4,235,898 | 11/1980 | Watanabe et al. | 424/245 |
| 4,252,695 | 2/1981 | Homma et al. | 252/547 |

OTHER PUBLICATIONS

Inorganic Chemistry 16, 1934 (1977).

*Primary Examiner*—P. E. Willis, Jr.
*Attorney, Agent, or Firm*—Richard C. Witte; John V. Gorman; Douglas C. Mohl

[57] ABSTRACT

Metal salts of pyridinethione useful in shampoos, creme rinses and other hair care compositions to deliver antidandruff benefits while not detracting as much as previous pyridinethione salts from the compositions' aesthetics. Compositions containing such salts are also included.

8 Claims, No Drawings

HAIR CARE COMPOSITIONS

CROSS-REFERENCE TO RELATED APPLICATION

This is a divisional of application Ser. No. 119,347 filed Feb. 7, 1980 now U.S. Pat. No. 4,345,080.

TECHNICAL FIELD

The present invention is related to metal salts of pyridinethione which are in crystalline form and possess a geometry and particle size which make the crystals more compatible with a composition matrix.

BACKGROUND ART

The use of pyridinethione salts as antidandruff agents in shampoos and hair rinses is well known. U.S. Pat. No. 3,236,733, Feb. 22, 1966 to Karsten et al discloses detergent compositions containing such salts. Barnett, B. L., et al, "Structural Characterization of Bis(N-oxypyridine-2-thionato)Zinc(II)," *Inorganic Chemistry*, 16, 1834, [1977] discloses recrystallizing zinc pyridinethione crystals from chloroform or dimethyl sulfoxide. Other references which disclose pyridinethione salts are U.S. Pat. No. 2,809,971, Oct. 15, 1957 to Bernstein et al; U.S. Pat. No. 3,753,916, Aug. 21, 1973 to Parran; U.S. Pat. No. 3,761,418, Sept. 25, 1973 to Parran.

While it is known to use pyridinethione salts in hair care compositions the prior art does not indicate whether the salts are compatible with all components which may be present in a composition. Included among components which may be present in shampoos and other hair care compositions are those which make the compositions more aesthetically appealing. Aesthetics are important in encouraging a consumer to purchase a product as well as continue using the product after purchase.

One aesthetic characteristic which has found wide acceptance is pearlescence. This is quite often achieved through the use of material such as ethylene glycol distearate. The pyridinethione salt materials available up to this time have substantially interfered with the ability of pearlescent material to deliver acceptable pearlescence. This has been due, in all likelihood to the materials being in the shape of cubes and rods and of small size. The recrystallized material of Barnett et al supra, while allowing pearlescence, has been found to be less acceptable than the crystals of the present invention in finished compositions.

It is therefore an object of the present invention to provide pyridinethione salt crystals which interfere less with the pearlescent material than do prior art materials.

It is another object of the present invention to provide antidandruff compositions containing such crystals.

These and other objects will become obvious from the detailed description which follows.

DISCLOSURE OF THE INVENTION

The present invention relates to pyridinethione salt crystals which are predominantly flat platelets having a mean sphericity less than about 0.65 and a median particle size of at least about $2\mu$ diameter, expressed as the equivalent diameter of a sphere of equal volume. Compositions containing such crystals are also part of the present invention.

DETAILED DESCRIPTION OF THE INVENTION

Pyridinethione Salt Crystals

The present invention is concerned with heavy metal, magnesium or aluminum salts of 1-hydroxy-2-pyridinethione which has the following structural formula in tautomeric form, the sulfur being attached to the No. 2 position in the pyridine ring.

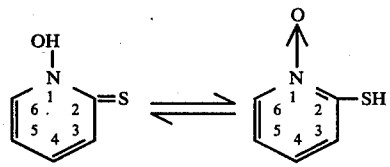

The metal salts represent substitution of the metal cation for the hydrogen of one of the tautomeric forms. Depending, of course, on the valence of the metal involved there may be more than one of the pyridinethione rings in the compound. Suitable heavy metals include zinc, tin, cadmium and zirconium.

The present pyridinethione salt crystals are predominantly flat platelets which have a mean sphericity less than about 0.65, preferably between about 0.20 and about 0.65 and a median particle size of at least about $2\mu$ diameter, expressed as the median equivalent diameter of a sphere of equal volume. It is preferred that the mean particle size be not greater than about $15\mu$, measured on the same basis. The median diameters are on a mass basis with 50% of the mass of particles falling on either side of the value given.

The diameter of a sphere of equivalent volume for a particle can be determined by a variety of sedimentation techniques which are based on Stokes' Law for the settling velocity of a particle in a fluid. Such techniques are described in Stockham, J. D. and Fochtman, E. G., *Particle Size Analysis*, Ann Arbor Science, 1978, incorporated herein by refernce. An approach for determining the median equivalent spherical diameter based on volume, $d_v$, is shown in Example II.

The sphericity of a particle is also described by Stockham and Fochtman at page 113 as $$\psi = \left(\frac{d_v}{d_s}\right)^2$$

where $d_v$ is the diameter of a sphere of equivalent volume, supra, and $d_s$ is the diameter of a sphere of equivalent area. In the present invention $$\text{the mean sphericity} = \left(\frac{\bar{d}_v}{\bar{d}_s}\right)^2 \text{ or}$$

surface area of spheres having equivalent volume distribution divided by the actual surface area of particles as measured.

A technique for determining actual surface area is shown in the examples using the BET technique described by Stockham and Fochtman at page 122.

Compositions Containing the Pyridinethione Metal Salts

The pyridinethione metal salts of the present invention are useful in a variety of hair care compositions as antidandruff aids. The salts are generally present at a level of from about 0.2% to about 4.0%, preferably from about 0.3% to about 2.0%, even more preferably from about 1% to about 2% in some compositions. Included among the hair care compositions are shampoos, creme rinses, hair tonics and many others. Shampoos are the preferred compositions and components generally found in such compositions are given below.

Surfactant

One essential component of the antidandruff shampoos herein is a surfactant. The term "surfactant" as used herein is intended to denote soap and nonsoap surfactants. The surfact component comprises from about 10% to about 50% by weight of the composition, preferably 10% to about 20%.

Any nonsoap surfactant is suitable for use including anionic, nonionic, amphoteric and zwitterionic types. Cationic surfactants may also be used, but these are not preferred in the shampoos of the present invention due to their irritaiton potential.

Examples of suitable soaps are the sodium, potassium, ammonium and alkanol ammonijm salts of higher fatty acids (those having 10–20 carbon atoms). Anionic nonsoap surfactants can be exemplified by the alkali metal salts of organic surfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 darbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodexocy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl)phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide, dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals ocntaining from about 8 to about 20 carbon atoms, from 0 to about 10 ethylene oxide moieties and from 0 to 1 glyceryl moiety. Examples include:
octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

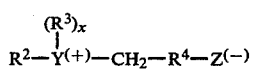

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.
Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-(P,P-dimethyl-P-dodecylphosphonio)-propane-1-phosphonate; and
5-[N,N-di(3-hydroxypropyl)-N-hexadecylammonio]-2-hydroxyhydroxypentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from 8 to about 18 carbon atoms and one contains an anionic water solubilizing group, e.g., carboxy, sulfonate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the tradename "Miranol" and described in U.S. Pat. No. 2,528,378.

Many cationic surfactants are known to the art. By way of example, the following may be mentioned:
dodecyltrimethylammonium chloride;
nonylbenzylethyldimethylammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride
dilauryldimethylammonium chloride; and
stearalkonium chloride.

Many additional nonsoap surfactants are described in McCUTCHEON'S, DETERGENTS AND EMULSIFIERS, 1979 ANNUAL, published by Allured Publishing Corpoiration, which is incorporated herein by reference.

The above-mentioned surfactants can be used alone or in combination in the shampoo compositions of the present invention.

Pearlescent Material

Another desirable component of the shampoos herein is a pearlescent material. Such materials are well known in the art and include bismuth oxychloride, stearic monoethanolamide, ethylene glycol monostearate or distearate, guanine and titanium dioxide coated mica. A pearlescent material is generally present at a level of from about 0.1% to about 6%, preferably form about 0.5% to about 5%.

Aqueous Carrier

The shampoos herein are preferably in the form of liquids or creams in which water is the principal diluent. The level of water in the compositions is typically from about 35% to about 90% by weight.

Optional Components

The antidandruff shampoos herein can contain a variety of non-essential optional ingredients suitable for rendering such compositions more stable and desirable. Such conventional optional ingredients are well known to those skilled in the art, e.g., preservatives such as benzyl alcohol, methyl paraben, propyl paraben and imidazolidinyl urea; thickeners and viscosity modifiers such as coconut ethanol amide, sodium chloride, sodium sulfate, carboxymethylcellulose, methylcellulose, polyvinyl alcohol, and ethyl alcohol; pH adjusting agents such as citric acid, succinic acid, phosphoric acid, sodium hydroxide, sodium carbonate, etc.; suspending agents such as magnesium/aluminum silicate; perfumes, dyes; and, sequestering agents such as disodium ethylenediamine tetraacetate.

Minor ingredients such as perfumes, dyes and coloring agents can also be added to the instant compositions to improve their consumer acceptability. If present, such agents generally comprise from about 0.1% to 2.0% by weight of the composition. The pH of the shampoos herein is generally from about 3 to about 9.

Other Hair Care Compositions

Creme rinses, hair tonics and other hair care compositions as well as shampoos may contain the pyridinethione salts of the present invention. These compositions may contain a variety of other components including some of those described supra for shampoos. Creme rinses generally contain a cationic surfactant similar to those described supra, particularly stearalkonium chloride and ditallow dimethyl ammonium chloride at a level of from about 0.1% to about 5%, preferably from about 0.5% to about 2%.

METHOD OF MANUFACTURE

The pyridinethione salt crystals may be made in a variety of ways. A preferred method is to react a soluble salt of the desired metal with, for example, an alkali metal pyridinethione salt in a surfactant medium. A suitable method is described in the examples which follow.

The hair care compositions containing the pyridinethione salt crystals may be made using techniques well known in the art.

INDUSTRIAL APPLICABILITY

The pyridinethione salts and compositions containing them are useful in combating dandruff. Such compositions are used in a conventional manner.

The following Examples further describe and demonstrate the preferred embodiments within the scope of the present invention. The Examples are given solely for the purpose of illustration and are not to be construed as limitations of the present invention as many variations thereof are possible without departing from its spirit and scope. Unless otherwise indicated, all percentages herein are by weight.

EXAMPLE I

Zinc pyridinethione salt crystals of the present invention were made using the following procedure.

A first mixture was prepared by combining 14.7 parts of zinc sulfate, 21.7 parts of a 29% aqueous solution of sodium alkyl sulfate and 8.6 parts of water in a mix tank. This mixture was heated to 95° C.

A second mixture was prepared by combining 35 parts of a 40% aqueous solution of sodium pyridinethione with 20 parts of a 29% aqueous solution of sodium alkyl sulfate in a mix tank. This second mixture was also heated to 95° C.

The first mixture was added to the second mixture resulting in the formation of zinc pyridinethione crystals which were washed and collected.

The total batch size, the combined mixtures, was 2500 grams.

EXAMPLE II

The crystals of zinc pyridinethione made according to Example I were evaluated to determine their particle size and sphericity.

The median equivalent spherical diameter based on volume (particle size) was determined by means of a SediGraph 500 D Particle Size Analyzer supplied by Micrometrics Instrument Corporation.

The SediGraph 5000 D determines, by means of X-ray absorption, the concentration of particles remaining at decreasing sedimentation depths as a function of time. Stokes' Law relates the measured equilibrium velocity of a particle falling through a viscous medium to its equivalent spherical diameter (ESD).

$$ESD = \left[ \frac{18 \cdot \eta \cdot v}{(\rho - \rho_o)g} \right]^{\frac{1}{2}}$$

$\eta$ = liquid viscosity
$v$ = equilibrium velocity
$\rho_o$ = liquid density
$g$ = gravitational acceleration
$\rho$ = particle density $v$ is determined from the Sedigraph while the other variables are available from reference sources or obtained experimentally. In the present analysis water was the liquid and the liquid viscosity was 0.76 cp.

The density of ZPT particles is known to be about 1.81 g/cc, (Barnett, B. L., et al, "Structural Characterization of Bis-(N-oxypyridine-2-thionato) Zinc (II)", *Inorganic Chemistry* 16, 1934, [1977]), incorporated herein by reference.

The median equivalent spherical diameter based on volume ($d_v$) of the crystals using Stokes' Law was determined to be 5.4μ.

This median equivalent spherical diameter was taken from the mass distribution of particles described in 1. below. The determination of a specific surface area based on equivalent spherical diameters was as follows:

1. A cumulative mass distribution of equivalent spherical diameters in μm was obtained using the SediGraph instrument described previously. The rate for the instrument was 866 and the starting diameter of 100 μm.

2. The cumulative mass distribution was divided into equal logarithmic intervals in μm. The sizes of the intervals are shown in the following table.

3. The cumulative mass distribution at each equal logarithmic interval was determined.

4. The diameter at the centerpoint of each interval was determined.

5. The value of the cumulative mass percent distribution at the centerpoints of the intervals was determined.

6. The value of the differential mass percent distribution was then determined.

7. The amount of material for each interval was determined, assuming that there was a total of one gram which was evaluated. These values are the values in 6, above, divided by 100.

8. The assumed spherical particle surface area of the material contained in each interval was calculated using diameters equal to the centerpoints of the intervals. Therefore, the calcualtion for a particular interval, i, is $$A_i = \frac{\text{(Mass contained in interval } i\text{)}}{\text{(Mass of sphere with diameter } d_i\text{)}} \times$$

(Surface area of sphere with diameter $d_i$)

$$A_i = \frac{\text{Mass contained in interval } i}{\rho \, 4/3 \, \pi \left(\frac{d_i}{2}\right)^3} (d_i)^2 \pi = \frac{6}{\rho} \frac{\text{mass}}{d_i}$$

$A = \Sigma_i A_i =$ Surface area/g assuming spheres

All of the above data are shown in the following table. The numerical column headings correspond to the numbers above.

| 2 | 3 | 4 | 5 | 6 | 7 | 8 |
|---|---|---|---|---|---|---|
| 1.59 | 0. | | | | | |
| | | 1.78 | 0.5 | 0.5 | 0.005 | 0.009 |
| 2.00 | 1.0 | | | | | |
| | | 2.28 | 2.5 | 2.0 | 0.020 | 0.029 |
| 2.52 | 4.0 | | | | | |
| | | 2.87 | 7.0 | 4.5 | 0.045 | 0.052 |
| 3.17 | 10.0 | | | | | |
| | | 3.59 | 16.0 | 9.0 | 0.090 | 0.083 |
| 4.00 | 22.0 | | | | | |
| | | 4.52 | 32.0 | 16.0 | 0.160 | 0.118 |
| 5.04 | 42.0 | | | | | |
| | | 5.70 | 55.0 | 23.0 | 0.230 | 0.134 |
| 6.35 | 68.0 | | | | | |
| | | 7.18 | 76.0 | 21.0 | 0.210 | 0.097 |
| 8.00 | 84.0 | | | | | |
| | | 9.04 | 88.5 | 12.5 | 0.125 | 0.046 |
| 10.08 | 93.0 | | | | | |
| | | 11.4 | 95.0 | 6.5 | 0.065 | 0.019 |
| 12.7 | 97.0 | | | | | |
| | | 14.4 | 98.0 | 3.0 | 0.030 | 0.007 |
| 16.0 | 99.0 | | | | | |
| | | 18.1 | 99.5 | 1.5 | 0.015 | 0.003 |
| 20.2 | 100.0 | | | | | |
| | | 22.8 | 100.0 | 0.5 | 0.005 | 0.001 |
| 25.4 | 100.0 | | | | | |
| | | | TOTAL - 100.0 | | 1.000g | 0.598 m²/g |

The specific surface area for the crystals was determined by means of a B.E.T. surface area analysis using nitrogen gas. The B.E.T. analysis showed the crystals to have a specific surface area of 2.39 m²/g.

The sphericity was then determined as follows:

$$\psi = \frac{\text{area per g calculated for assumed spherical distribution}}{\text{area per g from } B.E.T. \text{ measurement}}$$

$$\psi = \frac{0.598}{2.39} = 0.25$$

EXAMPLE III

A shampoo composition having the following formula was prepared.

| Component | Level |
|---|---|
| Ammonium Alkyl Sulfate (29% Aqueous solution) | 55.25% |
| Zinc Pyridinethione Crystals of Example I | 2.0 |
| Coconut Monoethanolamide | 3.0 |
| Ethylene Glycol Distearate | 5.0 |
| Sodium Citrate | 0.5 |
| Citric Acid | 0.2 |
| Color Solution | 0.1 |
| Perfume | 0.5 |
| Water | q.s.100.00% |

The pearlescence of this composition was better than an identical composition containing prior art zinc pyridinethione particles having a mean sphericity of about 0.75 and a mean equivalent spherical diameter based on volume of about 1.25μ.

EXAMPLE IV

The following shampoo is prepared.

| Component | Level |
|---|---|
| Triethanolamine Alkyl Sulfate (35% Aqueous Solution) | 50.0% |
| Triethanolamine | 3.0 |
| Coconut Monoethanolamide | 2.0 |
| Magnesium/Aluminum Silicate | 0.5 |
| Hydroxy Methyl Cellulose | 0.6 |
| Zinc Pyridinethione crystals of Example I | 2.0 |
| Color Solution | 0.1 |
| Perfume | 0.3 |
| Water | q.s.100.0% |

EXAMPLE V

The following cream shampoo is prepared.

| Component | Level |
|---|---|
| Sodium Alkyl Glyceryl Sulfonate | 60.0% |
| Sodium Chloride | 5.0 |
| Sodium N—Lauroyl Sarcosinate | 12.0 |
| N—Cocoyl Sarcosine Acid | 1.0 |
| Lauric Dethanolamide | 2.0 |
| Zinc Pyridinethione of Example I | 2.0 |
| Perfume | 0.5 |
| Color Solution | 0.12 |
| Water | q.s.100.00% |

EXAMPLE VI

The following creme rinse is prepared.

| Component | Level |
|---|---|
| Stearalkonium Chloride | 0.75% |
| Stearyl Alcohol | 0.5 |
| Zinc Pyridinethione of Example I | 0.3 |
| Cetyl Alcohol | 0.5 |
| Polyoxyethylene(2)Cetyl Ether | 0.8 |
| Sodium Chloride | 0.25 |
| Color Solution | 0.2 |
| Perfume | 0.25 |
| Water | q.s.100.00% |

What is claimed is:

1. Hair care compositions which contain from about 0.2% to about 4.0% of heavy metal, magnesium or aluminum pyridinethione salt crystals which are predominantly flat platelets having a mean sphericity less than about 0.65 and a median equivalent spherical diameter based on volume of at least about 2μ but less than about 15μ.

2. A hair care composition according to claim 1 in the form of a shampoo which additionally contains from about 10% to about 50% of a surfactant.

3. A shampoo according to claim 2 wherein the surfactant is an alkyl sulfate salt.

4. A shampoo according to claim 3 in the form of a lotion, which additionally contains from about 35% to about 90% water and wherein the alkyl sulfate salt is ammonium alkyl sulfate.

5. A shampoo according to claim 4 which additionally contains from about 0.1% to about 6.0% of a pearlescent material.

6. A hair care composition according to claim 1 in the form of a creme rinse and which additionally contains from about 0.1% to about 5.0% of a cationic surfactant and from about 95% to about 99% water.

7. A creme rinse according to claim 6 which additionally contains from about 0.5% to about 5.0% of a pearlescent material.

8. A creme rinse according to claim 7 wherein the cationic surfactant is selected from the group consisting of stearalkonium chloride, ditallow dimethyl ammonium chloride and mixtures thereof.

* * * * *